(12) United States Patent
Miga et al.

(10) Patent No.: US 9,767,573 B2
(45) Date of Patent: Sep. 19, 2017

(54) SYSTEM AND METHOD FOR CORRECTING DATA FOR DEFORMATIONS DURING IMAGE-GUIDED SURGICAL PROCEDURES

(75) Inventors: Michael I. Miga, Franklin, TN (US); Prashanth Dumpuri, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 13/574,624

(22) PCT Filed: Jan. 21, 2011

(86) PCT No.: PCT/US2011/021990
§ 371 (c)(1),
(2), (4) Date: Sep. 13, 2012

(87) PCT Pub. No.: WO2011/091218
PCT Pub. Date: Jul. 28, 2011

(65) Prior Publication Data
US 2012/0330635 A1    Dec. 27, 2012

Related U.S. Application Data

(60) Provisional application No. 61/297,336, filed on Jan. 22, 2010.

(51) Int. Cl.
*G06T 7/33* (2017.01)
*G06G 7/60* (2006.01)
*A61B 5/00* (2006.01)

(52) U.S. Cl.
CPC ............................ *G06T 7/33* (2017.01); *A61B 5/00* (2013.01); *G06G 7/60* (2013.01)

(58) Field of Classification Search
CPC .................................. G06G 7/60; A61B 5/00
See application file for complete search history.

(56) References Cited

U.S. PATENT DOCUMENTS

2004/0019274 A1    1/2004  Galloway, Jr. et al.
2008/0123927 A1    5/2008  Miga et al.

OTHER PUBLICATIONS

Cash et al., Concepts and preliminary data toward the realization of image-guided liver surgery, J Gastrointestinal Surgery, vol. 11(7), p. 844-859, 2007.

(Continued)

*Primary Examiner* — G. Steven Vanni
(74) *Attorney, Agent, or Firm* — Nixon Peabody LLP; Eduardo J. Quinones

(57) ABSTRACT

Systems and methods for collecting and processing physical space data for use while performing an image-guided surgical (IGS) procedure are provided. The system and method includes obtaining a computer model of a non-rigid structure of interest in a patient and performing a rigid alignment of the computer model and surface data in a patient space associated with at least a portion of the non-rigid structure. The system and method also include computing a deformation of the computer model that provides a non-rigid alignment of the computer model and surface data, the deformation computed using a set of boundary conditions defined for each node of the computer model based on the rigid alignment and a kernel function. Additionally, the system and method can include displaying data for facilitating the IGS procedure based on the deformation.

6 Claims, 10 Drawing Sheets

(56) References Cited

OTHER PUBLICATIONS

King et al., "Tracking liver motion using 3-D ultrasound and a surface based statistical shape model", Proceedings of the IEEE Workshop on Mathematical Methods in Biomedical Image Analysis (2001), p. 145-152.

Platenik et al., "In vivo quantification of retraction deformation modeling for updated image-guidance during neurosurgery", IEEE Trans Biomed Eng (2002) 49(8): 823-835.

American Cancer Society, "Cancer Facts and Figures", American Cancer Society (2004) Atlanta, 60 pages total: 2 forepages, p. 1-56 and 2 after pages.

Antipolis, "Project-team epidaure: Epidaure, project images, diagnostic, automatique, robotique medical imaging, & robotics", INRIA 2003. (50 pages), 2 forepages and p. 1-48.

Ayache, "Epidaure: A research project in medical image analysis, simulation, and robotics at INRIA", IEEE Trans Med Imaging (2003) 22: 1185-1201.

Bao et al., "Ultrasound-to-computer-tomography registration for image-guided laparoscopic liver surgery", Surg. Endosc. (2005), vol. 19, p. 424-429.

Barnes et al., "A novel model-gel-tissue assay analysis for comparing tumor elastic properties to collagen content", Biomech Model Mechanobiol (2009), vol. 8, p. 337-343.

Barnes et al., "Development of a mechanical testing assay for fibrotic murine liver", Medical Physics (2007) 34 (11): 4439-4450.

Barnes, et al., "Development of a mechanical testing assay for modulus analysis of fibrotic murine livers", 6th International Conference on the Ultrasonic Measurement and Imaging of Tissue Elasticity, Santa Fe, New Mexico, (Nov. 2007), Abstract 060, p. 48.

Blackall et al., "A statistical model of respiratory motion and deformation of the liver", Medical Image Computing and Computer-Assisted Interventions, S. Verlag, Ed. Berlin (2001) 2208: 1338-1340.

Blumgart et al., "Surgical options in the treatment of hepatic metastases from colorectal cancer", Curr. Prob. Surg. (1995) 35: 336-413.

Bradley et al., "Surgical experience with hepatic colorectal metastasis", Am. Surg. (1999) 65: 560-567.

Cao, "Segmentation of medical images using level set-based methods", PhD. Dissertation, Electrical Engineering, Computer Engineering, and Computer Science Nashville: Vanderbilt University (2004). (151 pages), 15 of 151 total pages filed and considered, including p. i-ix and 1-3.

Cash et al., "Compensating for intraoperative soft-tissue deformations using incomplete surface data and finite elements", IEEE Transactions on Medical Imaging (2005) 24: 1479-1491.

Cash et al., "Concepts and preliminary data toward the realization of image-guided liver surgery", Gastrointest Surg (2007) 11: 844-859.

Clements et al., "Atlas-based method for model updating in image-guided liver surgery", SPIE Medical Imaging 2007: Visualization, Image Guided Procedures, and Modeling, San Diego, CA. (12 pages), p. 650917-650928.

Clements et al., "Organ surface deformation measurement and analysis in open hepatic surgery: Method and preliminary results from 12 clinical cases", IEEE Transactions on Biomedical Engineering (2011) 58(8): 2280-2289.

Clements et al., "Robust surface registration using salient anatomical features for image-guided liver surgery: Algorithm and validation", Medical Physics (2008) 35(6): 2528-2540.

Clements et al., "Salient anatomical features for robust surfaces registration and atlas-based model updating image-guided liver surgery," Ph.D. Dissertation, Vanderbilt University, Department of Biomedical Engineering (2009). (171 pages), p. i-xx and 1-151.

Cohnert et al., "Preoperative risk assessment of hepatic resection for malignant disease", World J. Surg. (1997) 21: 396-400.

Dematteo et al., "Anatomic segmental hepatic resection is superior to wedge resection as an oncologic operation for colorectal liver metastases", J. Gastrointest. Surg. (2000) 4: 178-184.

Dumpuri et al., "Comparison of pre/post-operative CT image volumes to preoperative digitization of partial hepatectomies: A feasibility study in surgical validation", SPIE Medical Imaging 2009: Visualization, Image-Guided Procedures and Modeling Conference. (7 pages), p. 726122-726128.

Dumpuri et al., "Model-updated image-guided liver surgery: preliminary results using intraoperative surface characterization", SPIE 2010: Medical Imaging Visualization, Image-Guided Procedures, and Modeling Conference. (7 pages), 7 pages beginning at p. 76251H.

Fredricks et al., "3D CT modeling of hepatic vessel architecture and volume calculation in living donated liver transplantation", Eur J Radiol (2004) 14: 326-333.

Hackworth et al., "A dual compute resource strategy for computational model assisted therapeutic interventions", SPIE Medical Imaging 2009: Visualization, Image-Guided Procedures, and Modeling (2009) 7261: 72612R1-7.

Hartkens et al., "Measurement and analysis of brain deformation during neurosurgery", IEEE Transactions on Medical Imaging (2003) 22: 82-92.

Hermoye et al., "Liver segmentation in living liver transplant donors: Comparison of semiautomatic and manual methods", Radiology (2005) 234: 171-178.

Jarnagin et al., "Improvement in perioperative outcome after hepatic resection: analysis of 1803 consecutive cases over the past decade", Ann. Surg. (2002) 236: 397-406.

Knaus et al., "System for laparoscopic tissue tracking", IEEE Symposium on Biomedical imaging, Washington, D.C. (2006). (4 pages), p. 498-503.

Lang et al., "Extended left hepatectomy—modified operation planning based on three-dimensional visualization and liver anatomy", Langenbecks Arch Surg. (2004) 389: 306-310.

Laurent et al., "Influence of postoperative morbidity on long-term survival following liver resection for colorectal metastases", Br. J. Surg., (2003) 90: 1131-1136.

Lorenson et al., "Marching cubes: A high resolution 3d surface construction algorithm", ACM Computer Graphics, (1987) 21: 163-169.

Matasuni et al., "Modally controlled free form deformation for non-rigid registration in image-guided liver surgery", Medical Image Computing and Computer-Assisted Interventions, S. Verlag, Ed. Berlin (2001) 2208: 1275-1278.

Maurer et al., "Registration of 3D images using weighted geometrical features", IEEE Transactions on Medical Imaging (1996) 15(6): 836-849.

Miga et al., "Intraoperative registration of the liver for image-guided surgery using laser range scanning and deformable models", Medical Imaging 2003: Visualization, Image-guided Procedures, and Display (2003): 350-359.

Miga, "The changing roles for soft-tissue modeling: Therapy guidance", Workshop on Clinical Image-Guided Therapy: Opportunities and Needs, Sponsored by the National Institutes of Health and National Center for Image-Guided Therapy, Washington D.C. (Mar. 2008). (1 page), p. 32.

Nabavi et al., "Image-guided therapy and intraoperative MRI in neurosurgery", Minimally Invasive Therapy & Allied Technologies (2000) 9: 277-286.

Nabavi et al., "Serial intraoperative magnetic resonance imaging of brain shift", Neurosurgery (2001) 48: 787-797.

Nimsky et al., "Intraoperative magnetic resonance tomography—experiences in neurosurgery", Nervenarzt (2000) 71: 987-994.

Nimsky et al., "Quantification of, visualization of, and compensation for brain shift using intraoperative magnetic resonance imaging", Neurosurgery (2000) 47:1070-1078.

Penney et al., "Registration of freehand 3D ultrasound and magnetic resonance liver images", Medical Image Analysis (2004) 8: 81-91.

Scheele et al., "Resection of colorectal liver metastasis", World J. Surg., (1995) 19: 59-71.

(56) References Cited

OTHER PUBLICATIONS

Schindl et al., "The value of residual liver vol. as a predictor of hepatic dysfunction and infection after major liver resection", Gut (2005) 54: 289-296.
Selle et al., "Analysis of vasculature of liver surgical planning", IEEE Trans Med Imaging (2002) 21:1344-1257.
Sheiner et al., "Treatment of metastatic cancer to the liver", Seminars in Liver Disease (1994) 14(2): 169-177.
Stevanovic et al., "Modeling contact between rigid sphere and elastic layer bonded to rigid substrate", IEEE Trans on Components and Package Technologies (2001) 24: 207-212.
Stone et al., "Surgical therapy for recurrent liver metastases from colorectal cancer", Arch Surg. (1990) 125: 718-722.
Sunthau et al., "A concept work for augmented reality visualization based on a medical application in liver surgery", Proc. of the ISPRS Commission V Symposium, Corfu, Greece, (2002): 274-280.
Yamamoto et al., "Pathologic support for limited hepatectomy in the treatment of liver metastases from colorectal cancer", Ann. Surg. (1995) 221: 74-78.

100

106

600

1000

SYSTEM AND METHOD FOR CORRECTING DATA FOR DEFORMATIONS DURING IMAGE-GUIDED SURGICAL PROCEDURES

CROSS-REFERENCE TO RELATED APPLICATIONS

This application is a §371 national stage entry of International Application No. PCT/US2011/021990, filed Jan. 21, 2011, which claims priority to U.S. Provisional Application No. 61/297,336, filed Jan. 22, 2010, both of which are hereby incorporated by reference.

STATEMENT REGARDING FEDERALLY SPONSORED RESEARCH

This invention was made with government support under Grant No. R21 EB007694-01 awarded by National Institutes of Health. The government has certain rights in the invention.

FIELD OF THE INVENTION

The present invention relates to systems and methods for image-guided procedures, and more specifically to systems and methods for correcting tissue data for deformations during image guided procedures.

BACKGROUND

The determination of an accurate image-to-physical space registration is a fundamental step in providing meaningful guidance information to surgeons via image-guided surgery (IGS). A significant body of research has been dedicated to the use of IGS techniques for neurosurgical applications and has resulted in several commercially available systems. A common feature of the IGS technology for neurosurgery is the use of point-based landmarks, via bone-implanted or skin-affixed fiducial markers, to provide the registration of image and physical space. The use of such point-based techniques is greatly facilitated in neurosurgical IGS by the rigid anatomy surrounding the tissues of interest (e.g., the skull). Unfortunately, the use of such point-based techniques is not applicable for open abdominal IGS due to the lack of rigid anatomical landmarks and the inability to preoperatively attach fiducial markers that will remain in a fixed position during the IGS procedure.

Since the use of rigid, point-based landmarks is not feasible for open abdominal IGS, surface-based techniques have been proposed to determine the registration between the preoperative images and the intraoperative presentation. For example, the iterative closest point (ICP) algorithm has traditionally been used to determine the transformation between the image-space surface of an organ and/or other soft tissues of interest. In ICP methods, the transformation is generally derived from preoperative image segmentations, and the intraoperative tissue surfaces. Intraoperative data for use in abdominal IGS is typically acquired using an optically tracked probe, a laser range scanner (LRS), or intraoperative ultrasound (iUS), and other methods.

The typical protocol for surface-based image-to-physical space registration in abdominal IGS begins with the selection of anatomical fiducial points in the preoperative image sets prior to surgery. The homologous physical-space location of these anatomical fiducials is then digitized during the surgical procedure such that a point-based initial alignment registration can be performed. The point-based registration serves to provide a reasonable initial pose for the ICP algorithm, which is used to register the tissue surfaces derived from preoperative images and the intraoperative data.

However, the surface alignment provided by the ICP algorithm is highly dependent on the initial pose of the tissue surfaces. Therefore, gross errors in the initial alignment provided by the point-based registration can result in erroneous surface alignments. While initial pose is important, another aspect of misalignment that can confound the ICP algorithm is the presence of intraoperative deformation. That is when organ and other soft tissues are surgically presented intraoperatively for surface acquisition (such as by laser range scanning), the soft tissues have generally undergone deformation due to routine surgical manipulation. Errors associated with pose or deformation introduced into any form of rigid registration will generally compromise the guidance information relayed to the surgeon. Some examples of soft tissue deformation due to surgical manipulation are (1) gravity-induced deformations of the liver due to reorientation of the organ with respect to the direction of gravity in the open-abdomen, (2) the effects of tissue mobilization and organ packing, and (3) changes in organ perfusion.

SUMMARY

Figure 1:
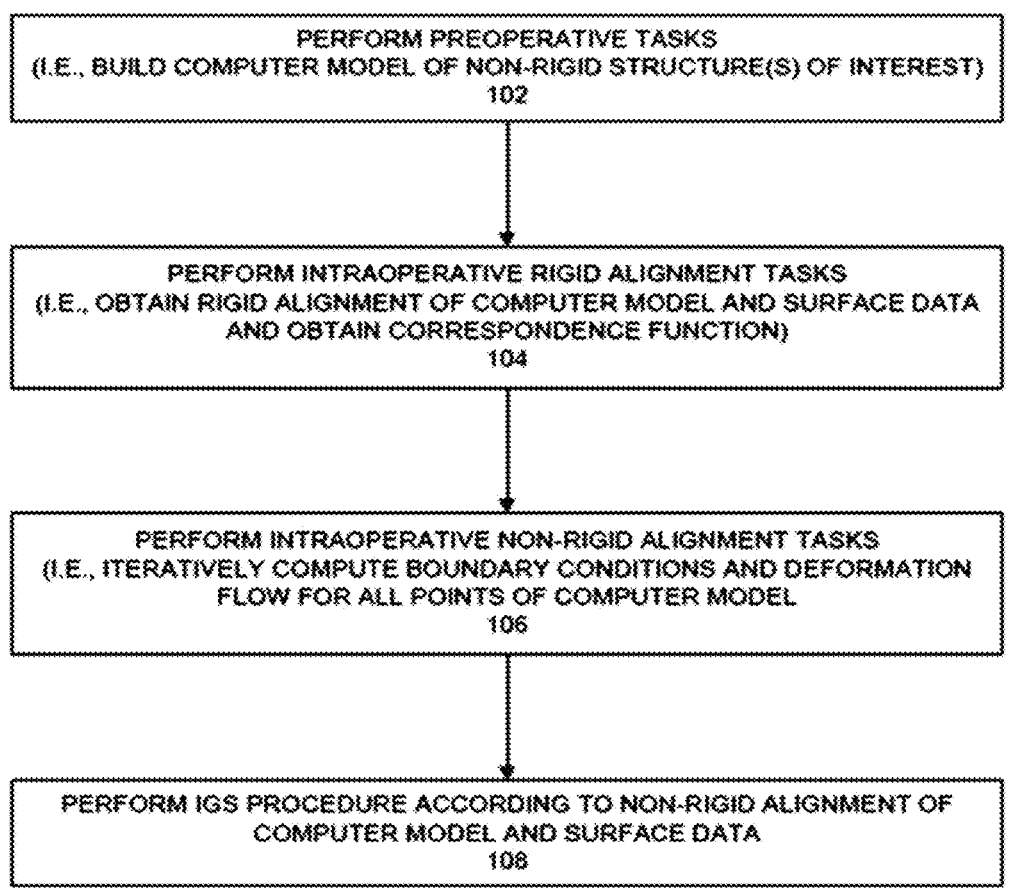
FIG. 1 shows a flow chart for performing IGS procedures in accordance with an embodiment of the invention.

Embodiments of the invention concern systems and methods for correcting tissue data for deformations during image guided procedures. In a first embodiment, a method is provided for collecting and processing physical space data for use while performing an image-guided surgical (IGS) procedure. The method includes the step of performing a rigid alignment of a computer model of a non-rigid structure of interest in a patient and surface data in a patient space associated with at least a portion of the non-rigid structure. The method also includes computing a deformation of the computer model that provides a non-rigid alignment of the computer model and surface data, the deformation computed using a set of boundary conditions defined for each node of the computer model based on the rigid alignment and a kernel function. The method can further include displaying data for facilitating the IGS procedure based on the deformation.

In a second embodiment, a system is provided for collecting and processing physical space data for use while performing an image-guided surgical (IGS) procedure. The system can includes a storage medium for storing a computer model of a non-rigid structure of interest in a patient. The system also includes at least one sensor device for generating at least surface data associated with the non-rigid structure and a processing element communicatively coupled to the storage medium and the sensor device. In the system, the processing element is configured for obtaining a rigid alignment of the computer model and surface data in a patient space associated with at least a portion of the non-rigid structure, computing a deformation of the computer model that provides a non-rigid alignment of the computer model and surface data, the deformation computed using a set of boundary conditions defined for each node of the computer model based on the rigid alignment and a kernel function. The system can additionally include a display device communicatively coupled to the processing element and configured for displaying data for facilitating the IGS procedure based on the deformation.

In a third embodiment, a computer-readable storage medium is provided, having stored thereon a computer program for collecting and processing physical space data for use while performing an image-guided surgical (IGS) procedure. The computer program has a plurality of code sections, the code sections executable by a computer to cause the computer to perform the steps of obtaining a computer model of a non-rigid structure of interest in a patient and performing a rigid alignment of the computer model and surface data in a patient space associated with the non-rigid structure. The code sections are also configured to cause the computer to perform the step of computing a deformation of the computer model that provides a non-rigid alignment of the computer model and surface data, the deformation computed using a set of boundary conditions defined for each node of the computer model based on the rigid alignment and a kernel function. Further, the code sections are also configured to cause the computer to perform the step of displaying data for facilitating the IGS procedure based on the deformation.

In the various embodiments, the displaying can further entail receiving image data associated with the computer model and locations in the patient space associated with the object and neighboring the object and transforming the computer model into the patient space based on the rigid alignment and the deformation. The displaying can also include computing reverse deformation displacement vector field values for each node of the computer model based on the deformation and calculating an envelope of additional reverse deformation vector field values for a portion of the patient space surrounding the deformed computed model. Additionally, the displaying can include transforming the locations into a computer model space of the computer model based on the non-rigid alignment and the reverse deformation displacement vector field values and calculating coordinates in an image space of the image data for the transformed locations.

DETAILED DESCRIPTION

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention provide systems and method for correcting tissue data for deformations occurring during IGS procedures. A general flow of an exemplary method is illustrated in FIG. 1. FIG. 1 is a flowchart showing steps in an exemplary method for performing an IGS procedure in accordance with an embodiment of the invention. As shown in FIG. 1, the method 100 includes a preoperative phase at block 102, an intraoperative rigid alignment phase at block 104, and an intraoperative non-rigid alignment, phase at block 106. Following or concurrently with these phases, the IGS procedure can be performed at block 108.

As described above, the method 100 begins at block 102. At block 102, preoperative tasks are performed. The preoperative tasks include building a computer (i.e., mathematical) model of at least the soft tissues, organs, or other non-rigid structures of interest in the patient. Although the various embodiments of the invention will be described with respect to IGS procedures for non-rigid structures, the invention is not limited in this regard. Rather, the various embodiments of the invention are equally applicable in IGS procedures involving one or more rigid structures in a patient (e.g., bones) or a combination of rigid and non-rigid structures.

The computer model can be built using several sets of preoperative data. For example, preoperative images of the non-rigid structures are acquired and processed to generate a computer model that describes at least the geometry of the non-rigid structures of interest. These can be acquired using two or three dimensional imaging techniques. For example, some imaging techniques include computerized tomography (CT), magnetic resonance (MR), and ultrasound imaging techniques, to name a few. However, the various embodiments of the invention are not limited in this regard and any other imaging techniques can be used. Further, the computer model can also be configured to include any other possible data, such as physical data (e.g., elastic properties, thermoelastic properties, etc. and other aspects relevant to the mechanics of the non-rigid structure) that could be necessary to calculate deformation within the operative environment. Based on the data obtained, tasks for building the computer model can be performed. For example, a distribution of deformation shapes to be used in the fitting process can be generated. Also, preoperative image analysis can be performed in order to enhance feedback or computer mesh generation. Further, pre-operative generation of mathematical functions to assist fitting can be performed. Also, a designation/segmentation of shapes or partial surfaces of the non-rigid structures of interest can be performed. However, the invention is not limited in this regard and other tasks can be performed to enhance the imaging or fitting processes of method 100.

Although the various embodiments will be described primarily with respect, to surfaces of non-rigid tissues that are exposed during medical procedures, such as the exterior surfaces of organs, tumors, and other biological tissues, the various embodiments are not limited in this regard. Rather, a "surface", as used herein, can refer to either external or internal features associated with a non-rigid structure of interest. That is, in addition to external surfaces, the surfaces referred to herein can include internal surfaces or features defined by a boundary between different structures or different types of tissues. For example, a boundary or division between cancerous and healthy tissues can define a surface. In another example, the division between liver vasculature and a parenchyma of a liver can also define a surface. In another example, it could represent the surface or feature point of a synthetic structure inserted within the organ that can be located via some localization method.

In the various embodiments of the invention, this preoperative phase can either be performed on one or more computing systems. Further, the preoperative phase can be performed on the same or different computing systems as the intraoperative tasks described below are performed. An exemplary computing system could include software packages configured to solve large sparse matrices that can be used for mathematical model solutions. Such a computing system could also include software libraries that provide computer model mesh/grid generation. Further, such a computing system can include both standard and customized mathematical and simulation libraries. Once the preoperative phase at block 102 has been completed, method 100 continues to block 104.

At block 104, intraoperative rigid alignment tasks are performed. That is, intraoperative surface data for one or more portions of the non-rigid structures is obtained intraoperatively and the counterpart surface data within image-space is obtained and aligned with a mathematical transformation. Thereafter the surface data of the non-rigid structure and the computer model are initially aligned. In some embodiments of the invention, a best-aligned method can be used. As used herein, a best-aligned method is an alignment of the image data and the non-rigid structures so that features on the surface of the non-rigid structure are positioned as close as possible to their image-space counterparts after the conclusion of the alignment process. However, the various embodiments of the invention are not limited in this regard and other alignment schemes can be used as well as internal substructures or feature points. Once this rigid alignment, is complete, the surface data and the computer model are aligned, without any deformation of the computer model, i.e. a rigid alignment. Such an alignment can be performed in a variety of ways. For example, an iterative method can be use to alter the position of one of the surface data and the computer model until an error between the surface data and the computer model is minimized.

Additional processing of the available geometric surface data can also be performed at block 106. Intraoperative surface data can be obtained in a variety of ways. For example, some methods include ultrasound, MR imaging, CT imaging, laser and/or other light-based strategies, swabbing with a tracked stylus, to name a few. However, the various embodiments of the invention are not limited in this regard and other methods can be used to obtain surface data. In many cases, the surface data obtained will only represent a portion of the non-rigid structure, i.e. a partial surface. For example, during a liver procedure, only the anterior portion of the liver may be exposed. Therefore, the surface data could be acquired using laser range scan technology which would limit geometric data to representing the anterior portion of the liver. In another example, the liver and a tumor may be partially exposed. However, the surface of interest may be a boundary between a tumor and the liver, an interior surface. In such cases, ultrasound imaging could be used to locate such interior surfaces of interest.

The surface data can also include noise or other errors that could affect alignment. Accordingly, in some embodiments of the invention, once the surface data is acquired, the surface data can be filtered or otherwise processed to reduce or eliminate of noise and/or other artifacts. Such methods are well known to those of ordinary skill in the art and will not be described here. In the various embodiments of the invention, such processing can be performed before or after the rigid alignment. In addition, in some cases where multiple surface data acquisitions from different methods are available and digitized in a common coordinate space, a composite surface can be used for alignment purposes.

Upon completion of the rigid alignment at block 104, an initial correspondence function is generated that associates each point from the surface data with a counterpart point on the non-rigid structure within image-space. That is, for each point in the surface data, a means is provided for identifying the corresponding point in the computer model. For example, a closest point operator can be used to select the point on the computer model that is closest to each point on the surface data. In the various embodiments of the invention, this correspondence function may be expressed as a table, a mathematical function, or any other method of describing a relationship between the spaces defined two sets of points. In some cases, the deformation observed in the surface data may result in the correspondence function associating points from non-corresponding surfaces of the computer model with points on the surface associated with the surface data. Accordingly, in some embodiments of the invention, the closest point operator can be refined or constrained to limit its search to corresponding surfaces. That is, the computer model and the surface data can be associated with designators that differentiate between the various surfaces of the non-rigid structure of interest. Accordingly, the search for corresponding points can be limited by such designators. For example, anterior surface nodes of surface data could be limited to the anterior surface nodes of the computer model, despite the fact that posterior surface nodes of the computer model are closer.

For purposes of obtaining a correspondence function, the various embodiments of the invention are not limited to closest point operator methods. Rather any other methods for obtaining correspondence or registration functions between two surfaces can be used in the various embodiments of the invention. For example, in some embodiments of the invention, corresponding points can be selected using a ray projection technique in which a ray is projected along a line perpendicular to a point on one surface and the corresponding point is selected to be the point that is intersected on the second surface.

Once the rigid alignment and a correspondence function are obtained at block 104, method 100 can proceed to block 106. At block 106, a set of boundary or point (internal and/or external) conditions, based on the rigid alignment at block 106 and the correspondence function of 104, and a displacement field of vectors in three dimensions is iteratively computed to perform a non-rigid alignment of the computer model to the surface data. That is a displacement field of vectors for deforming the computer model to fit the surface data is computed. The operations occurring in this block will be described below in greater detail with respect to FIG. 2. Once the non-rigid alignment tasks are completed at block 106, the IGS procedure can be performed at block 108.

Non-Rigid Alignment Phase

Figure 2:
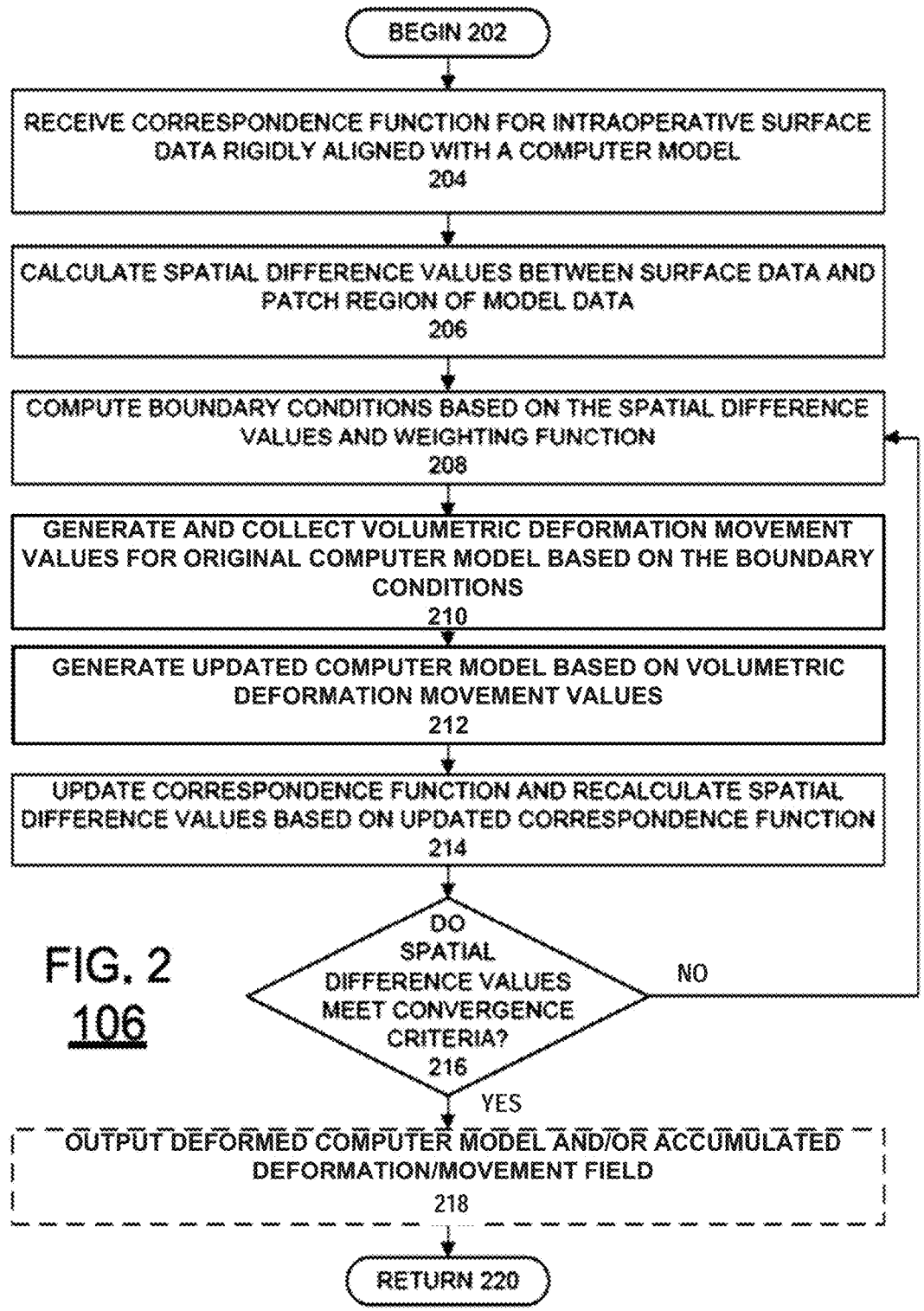
FIG. 2 is a flow chart of an exemplary method for performing a non-rigid alignment in accordance with and embodiment of the invention.

As described above, once a rigid alignment and a correspondence function are obtained at block 104, a non-rigid alignment can be performed at block 106. This is described below with respect to FIG. 2. FIG. 2 is a flow chart of an exemplary method 106 for performing a non-rigid alignment in accordance with and embodiment of the invention. Method 106 begins at block 202 and continues on to block 204. At block 204, the correspondence function for the computer model and the surface data is received. In addition to identifying corresponding points between the computer model and the surface data, the correspondence function also identifies a patch region of the computer model. That is, since the surface data can generally be obtained for only the exposed portion of non-rigid structure (although substructure designation is possible with additional instrumentation), a patch region is defined by the portions of the computer model corresponding to the surface data. Afterwards, at block 206, spatial difference values are computed for each node within the patch region. As used herein, the term "node" refers to the points of a computer model mesh used for performing a simulation.

Since the correspondence function received at block 204 is based on a rigid alignment (i.e., no deformation of the computer model), the alignment can result in the surface data having data points positioned inside and outside the geometry of the computer model. As a result, the spatial difference values obtained at block 206 are signed. Thus, a positive value would mean that the node on the computer model would need to be pushed outward to move towards corresponding surface data points, whereas a negative value would mean that the node on the computer model would need to be pushed inwards to move towards corresponding surface data points. This process embodies any such transform that moves the nodes on the computer model to points designated by the correspondence function.

Once the spatial difference values for the patch region are calculated at block 206, boundary or point (internal and/or external) condition values can be computed at block 208 for each available node of the computer model. In particular, for each node of the computer model, the boundary or point (internal and/or external) conditions is selected to be a weighted average of the spatial difference values associated with the node of interest and surrounding nodes. This provides a smooth set of boundary or point (internal and/or external) conditions. In some embodiments of the invention, the function can weight all spatial difference values equally. In other embodiments of the invention, the function can weight spatial difference values differently by using a spatial kernel function or any other functional/statistical relationship. For example, in one embodiment of the invention, a radial spatial function can be selected for generating weights. However, the various embodiments of the invention are not limited in this regard and other strategies could be used to generate weights for the spatial function that, treats boundary or point (internal and/or external) conditions.

Since only the patch region is associated with available surface data, the flanking regions of the computer model (i.e., portions of the computer model outside the patch region) will not have a corresponding point on the surface data designated. Accordingly, the nodes in these flanking regions are assigned a zero signed closest point distance. Therefore, during the process of averaging distances via a radial spatial kernel, the resulting boundary or point (internal and/or external) condition value for a node in the patch region can be less than its spatial difference value since zero distances from nodes of the flanking regions will be considered in the weighted average. Similarly, nodes that reside adjacent to the patch but in flanking regions will have signed distances from the nodes within the patch region as part of its weighted average, and will result in non-zero signed distances being applied to immediately flanking spatial regions.

The calculation of boundary condition values is not limited to the weighted average method described above. In other embodiments of the invention, other methods can be used. For example, one method is a non-uniformly weighted average based on the confidence levels of the closest, point operator used. Additionally, a portion of the computer model could be neglected in favor of allowing user-prescribed boundary or point (internal and/or external) conditions. Such a configuration can allow different portions of the computer model to deform differently. Further, the average values need not be based on a radial spatial kernel. Rather, a kernel based on a different, geometric structure, such as the shape of the non-rigid structures or substructures thereof can be used to define the points to the averaged. For example, organs such as the liver have different segments. Therefore, applying this kernel can be limited according to segments of the liver. Additionally, some tissues can have areas of high curvature. Accordingly, a parameterization of such surface variations can be used to provide geometric information associated with the computer model and could be used as part, of kernel design. In another example, the kernel can also be based on a shape corresponding to how the nodes are connected in the computer model. Another realization utilizes a partial differential equation representation of the organ surface structure to distribute the bound any or point (internal and/or external) conditions to flanking regions. This approach treats the surface as a single continuous domain or kernel and utilizes a partial differential equation to distribute boundary information. Other designs for generating a spatially distribution of displacements from the known surface data can also be used.

Once the boundary or point (internal and/or external) conditions are computed at block 208, a volumetric deformation step or displacement vector field of values is generated and collected at block 210 for the computer model. The boundary conditions computed at block 208 for each node can be considered to be a displacement occurring normal (i.e. perpendicular) to the organ surface as one potential correspondence realization. Thus, the sign of the resulting average values can be used to define a direction of motion during simulation. Further, the combination of differently signed spatial values effectively constrains movement of one or more portions of the computer model.

Therefore, at block 210, the boundary or point (internal and/or external) conditions from block 208 are used to define the normal displacement conditions (either pushing or pulling has been designated) for each node in an embodiment. These displacement conditions are then used during deformation simulations of the computer model with the computer model to simulate deformation and calculate a volumetric deformation step or three-dimensional displacement field vectors for the entire computer model. In the various embodiments of the invention, any simulation method can be used to solve partial differential equations associated with deformation mechanics, such as Finite Difference methods, Finite Volume Methods, Spectral Elements methods, Spline-Based Methods or Monte Carlo methods, to name a few. However the invention is not limited in this regard and other simulation or interpolative/extrapolative methods could also be used. In some embodiments of the invention, the simulation can be configured to specify true normal (out or in to the surface) displacements while allowing lateral slip/sliding along the surface (i.e. tangent to the surface). In addition to the boundary conditions, a simulation tuned for a particular physical model(s) can also be used during the simulation. For example, the simulation can be tuned with a linear elastic, hyperelastic, or viscoelastic constitutive law. However, the various embodiments of the invention are not limited in this regard and the simulation can be configured in other ways to capture one or more other physical aspects of the deformation. Further, the direction of displacement does not have to be normal, i.e. perpendicular; this just represents one embodiment. For example, the displacement direction could be modified to represent an average of normals in a given region of the model. Also, user-specified information may be available regarding displacement direction which could be used. For example, if a fiducial landmark in the image volume and on the available organ surface were apparent, displacement of that feature could represent a direct, application of the known direction based enforcing strict correspondence of that feature.

Once the volumetric deformation field values are generated at block 210, an updated computer model can be generated at block 212. In particular, the accumulated volumetric deformation field values are used to deform the positions of the nodes of the computer model. Afterwards, at block 214, the correspondence function is updated based on the updated computer model and a new set of spatial difference values are recalculated to determine if the simulation has converged or whether additional simulation is needed. Therefore, the spatial difference values are evaluated at block 216 to see if they meet, a convergence or stopping criteria at block 216. If the convergence or stopping criteria is met at block 216, a deformed computer model is output at block 218. Optionally, the accumulated deformation field values can also be output at block 218. The method 106 can then resume previous processing at block 220, including repeating method 106 if the non-rigid structure is farther deformed. Otherwise, method 106 computes repeats blocks 208 to 216, where the updated spatial difference values are used to compute a new set of boundary conditions for the next, iteration. Other realizations may involve a return to block 104 followed by block 106 in the event that the convergence or stopping criteria are not met. This allows for iterations that, involve both rigid and non-rigid phases to include embodiments with varying ordering.

The convergence or stopping criteria at block 216 can be defined in several ways. For example, the convergence criteria can comprise comparing an average, mean, or other measure of the updated spatial distance values to a threshold value. Thus, if the measure is less than the threshold value, convergence criteria is met and no further iterations are necessary. Alternatively or in combination with threshold value criteria, criteria can also be provided which compares the current and previous sets of spatial difference values to determine whether a further iteration should be performed. For example, the convergence criteria can comprise comparing or calculating a difference between the average, mean, or other measure of the current and previous spatial distance values. Thus, if the difference is less than a threshold value, convergence criteria is met and no further iterations are necessary. Further, in some embodiments of the invention, the convergence criteria can be that a number of iterations have occurred. However, the invention is not limited to the exemplary convergence or stopping criteria conditions described above. Rather, any type of convergence criteria conditions can also be used in the various embodiments of the invention.

In some embodiments of the invention, the kernel used to generate weights can be adjusted at each successive iteration. For example, in the case of a radial kernel function embodiment, the radius size can be reduced over time to prevent excessive deformation. Such a change can be linear or non-linear. Further, the kernel function can also vary spatially. For example, in the case of a radial kernel function embodiment, the radius size can be larger for some portions of the computer model.

In the embodiment illustrated in FIG. 2, the original, un-deformed computer model is used to run the simulation for each successive iteration. However, the various embodiments of the invention are not limited in this regard. In some embodiments, the computer model can be deformed during each successive iteration. Thus, each iteration of the simulation can be based on an updated computer model, not the original computer model. Given that the application of boundary displacements as applied in a computer simulation can be dependent (by design) on the shape of the structures being modeled, this would result in different transformations. For example, if the boundary displacement was to move perpendicular to the surface of the structure being modeled at each iteration, allowing the shape to change at each successive iteration would change that trajectory. In addition, when one changes the shape of the structure being modeled at each iteration, the transmission of load to the successive transmission of shape can change. For example, applying the same level of force on to an area that is growing in geometric size results in elevated stresses and more considerable deformation. Therefore, taking into account changes to the shape of the modeled structure between iteration ultimately affects the accuracy of a biomechanical simulation. While the above speaks to varying forms of realizing geometric non-linear behavior in the deformation process, other embodiments may involve material non-linear behavior (i.e. varying constitutive behavior) as well as aspects related to fracture, tearing, or separation of materials. Additionally, in some embodiments of the invention, additional rigid alignment steps can be performed during successive iterations. For example, if an update computer model is used during each iteration, an additional rigid alignment can be performed during each iteration or after the final iteration is performed.

In some embodiments of the invention, the boundary conditions can also be applied in different ways during each iteration. For example, one exemplary method is to apply each new boundary condition to the original, undeformed geometry using the normal direction associated with the rigid structure shape. Another exemplary method is to apply boundary conditions to the undeformed geometry but vary the normal direction according to the non-rigid shape changes. In this scenario, an undeformed mesh could be used with a modified normal. Another exemplary method would be non-rigidly deform the organ, and rebuild the computer simulation with the new shape, and associate the normals with its new shape, Local Transform Generation Once the deformation displacement vector field is generated, as described above in FIG. 2, the preoperative image data could be easily deformed and the surgeon could use the new image space and data therein to proceed with the IGS. However, even when a substantially good alignment, is obtained, using an approach in accordance with the various embodiments of the invention or a conventional approach, IGS may not be straightforward.

First, since the deformation of the computer model would result, in deformation of one or more portions of the image data, details of the non-rigid structures can become distorted, blurred, or even obliterated. As a result, the surgeon may have difficulty in properly identifying the locations of some features of the non-rigid structure in image space. Second, accurately positioning of an instrument in image space can be difficult. For example, the deformation displacement vector field values and/or the deformed computer model could be used to identify the position of an instrument in image space. However, the inherent imperfection of the non-rigid alignment, between surface data and the computer model, errors in the surface data, and errors in the computer model can result in erroneous positioning of instruments in image space, and thus in patients. For example, if the non-rigid alignment results in a portion of the deformed computer model being positioned above the surface data, positioning the instrument according to the computer model may result in the instrument being positioned perfectly in image space, but above the surface of the non-rigid structure in patient space. Even worse, if the non-rigid alignment results in a portion of the deformed computer model being positioned below the surface data, positioning the instrument according to the computer model may result in the instrument being positioned perfectly in image space, but below the surface of the non-rigid structure in patient space, possibly damaging the non-rigid structure. The problems are compounded further when positioning of the instrument in image space causes both vertical and lateral positioning errors in patient space.

In view of such difficulties, another aspect of the invention provides a process for improving the transform for locating an instrument in image space. In the various embodiments of the invention, a local, non-rigid transform can be provided for mapping from the instrument position in patient-space to its appropriate position in image space. In particular, a mapping adjustment consisting of three individual local transforms volumes (change in x, y, and z position in image space) is provided. Using this mapping adjustment, the cursor representing instrument position can be moved in image-space to the appropriate image coordinate such that the proper image slice rendering is generated. This is conceptually illustrated in FIGS. 3A and 3B for one of the individual transforms as an example. This local transform is embodied with respect to instrument location in this description, however, any structure or landmark identified by the surgeon could undergo the transform process.

Figure 3A:
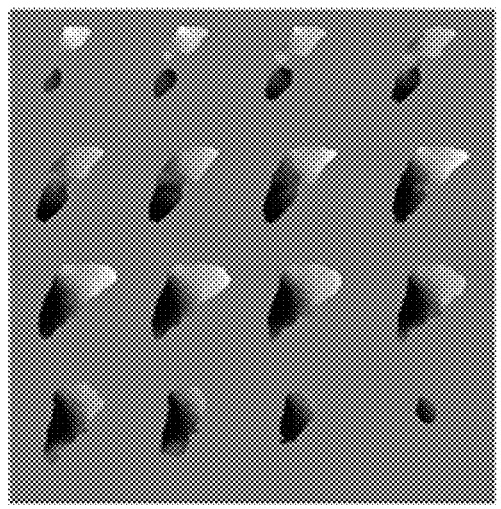
FIG. 3A shows transform maps resulting from a non-rigid alignment in accordance with an embodiment of the invention.
Figure 3B:
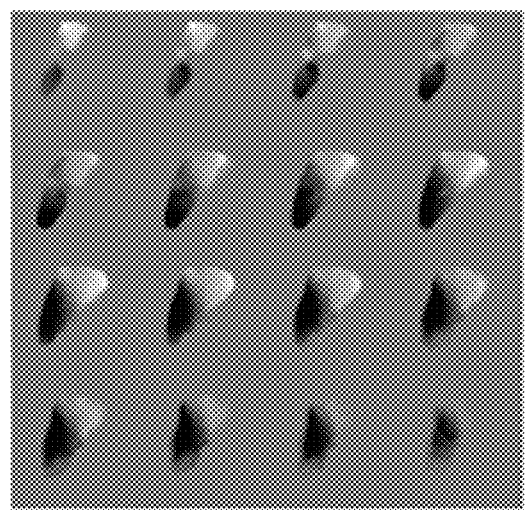
FIG. 3B shows the transform maps of FIG. 3A after applying an envelope in accordance with an embodiment of the invention.

FIGS. 3A and 3B illustrates an example of the local transform for the 'y' coordinate associated with correction before and after modifying the mapping in accordance with an embodiment of the invention. FIG. 3A shows the raw transform map as provided from the non-rigid alignment phase. As shown in FIG. 3A, transformations are only provided within the surface of the non-rigid structure. That is, the non-rigid alignment process provides a field of displacement vectors that allows for the displacement to be determined at all locations within the organ surface. To allow smooth transformations as a surgeon approaches the surface of the non-rigid structure in patient space, the various embodiments of the invention apply a diffusive process to the raw transform map of FIG. 3A. The resulting transforms after applying the diffusive process are shown in FIG. 3B. There are many ways to generate this transform envelope and a diffusive process is just one possible realization. Other embodiments could involve various averaging schemes, novel spatial kernels, filters, or a neighborhood functional form.

Upon generation of the full 3D local transformation mapping as shown in FIG. 3B, this transform would be ported to the IGS system. Thus, as data associated with instrument position is collected in patient space, the local transform is applied in image space to provide the appropriate shift. As a result, the proper cardinal image planes can be brought up on the IGS display and the surgeon gets a more accurate understanding of probe location. The results of this process are conceptually illustrated in FIGS. 4A and 4B. This embodiment allows for the pristine use of the original image data. It should be further noted that additional transforms of subsurface targets may need to be provided to the surgeon to provide accurate path planning to target.

Figure 4A:
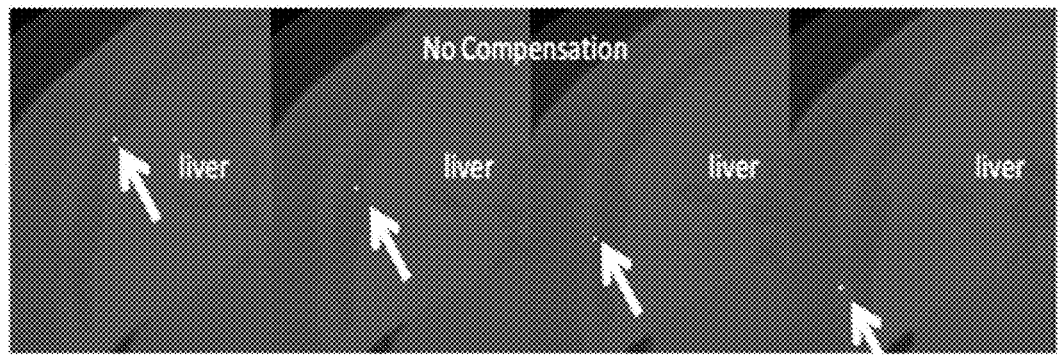
FIG. 4A is a diagram that conceptually illustrates the process whereby an image slice from the transverse plane through a liver is polled based on a mapping obtained after a rigid alignment.
Figure 4B:
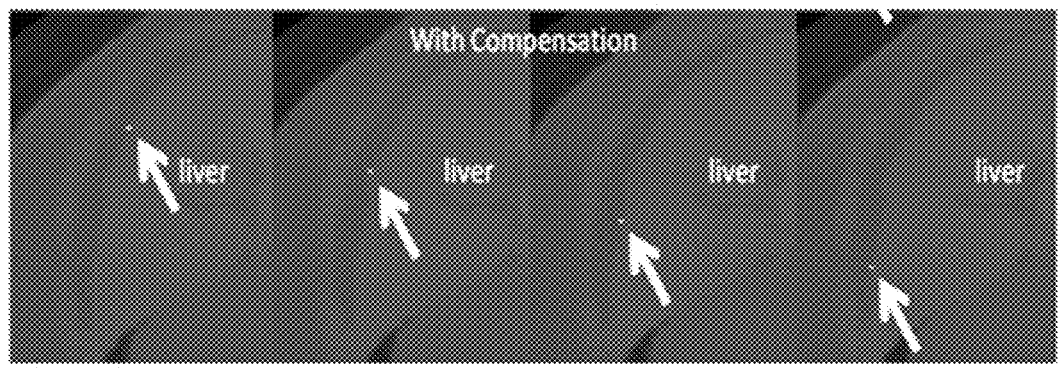
FIG. 4B is a diagram that conceptually illustrates the process whereby an image slice from the transverse plane through a liver is polled based on a rigid alignment and a local transform in accordance with an embodiment of the invention.

FIG. 4A is a diagram that conceptually illustrates the process whereby an image slice from the transverse plane through a liver is polled based on a mapping obtained without any adjustments, that is, the alignment provided by 104. FIG. 4B is a diagram that conceptually illustrates the process whereby an image slice from the transverse plane through a liver is polled based on the non-rigid of FIG. 2 and a local transform in accordance with an embodiment of the invention. For the purposes of simulating an IGS display in FIGS. 4A and 4B, a simulated stylus cursor is shown as being dragged across the liver in a medial to lateral direction on the physical patient, where the location of the stylus is shown on a transverse image as a dot with the arrow shown for location emphasis. As shown in FIG. 4A, it can be seen that because of imperfections in alignment using purely a rigid transformation (step 104 of FIG. 1), a cursor can fall well off the organ (liver in this case) in image space as the stylus is dragged across and reaches the more lateral surface regions of the organ. However, by applying a non-rigid mapping envelope in accordance with an embodiment of the invention, a cursor position can be corrected such that it does not inaccurately report its position as being off the organ (liver in this case) in image space but rather accurately portrays its location on the organ as the stylus is dragged across and reaches the more lateral surface regions of the organ.

Figure 5:
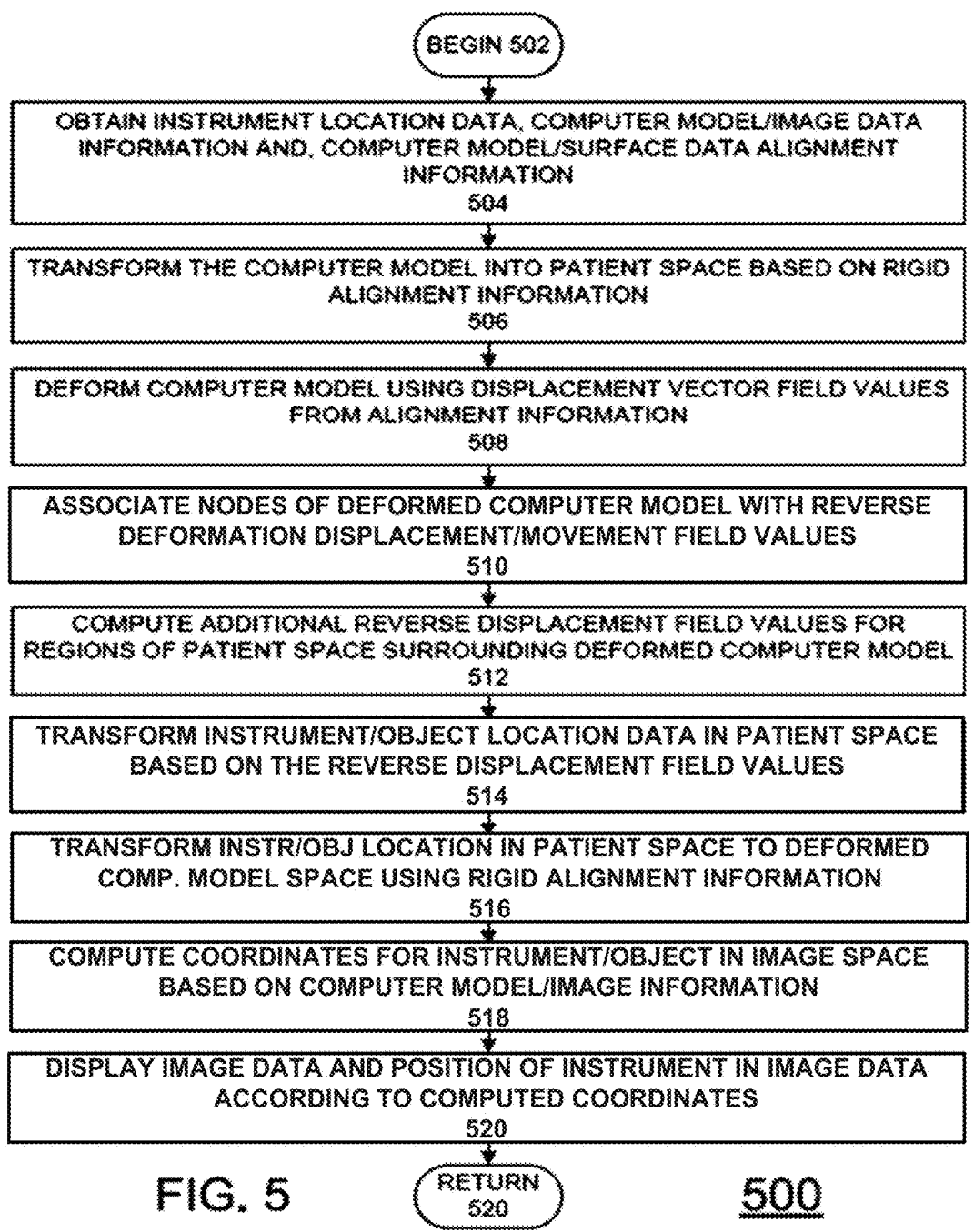
FIG. 5 is a flow chart of steps in an exemplary method for calculating a mapping adjustment for an instrument in image space in accordance with an embodiment of the invention.

One exemplary method for determining such mapping adjustments is described below with respect to FIG. 5. FIG. 5 is a flow chart of steps in an exemplary method 500 for calculating a mapping adjustment for an instrument in image space in accordance with an embodiment of the invention. Method 500 begins at block 502 and proceeds to block 504. At block 504, data sets for transforming an instrument in patient space to image space are obtained or received. In particular, a location of the instrument in patient space is received. Further, a computer model of the non-rigid structure is received, along with deformation displacement vector field values and the correspondence function for computer model and surface data after the rigid alignment, such as the deformation displacement vector field values and initial correspondence function obtained in FIG. 2. Furthermore, data associating the computer model and the image data is also received. In particular, the relationship between the nodes of the computer model and the voxels in the image data is received. Such a relationship can also be defined via an image/model correspondence function.

Once the data is received at block 504, the geometry of the computer model can be transformed in to patient space starting at block 506. First, at block 506 the rigid alignment information can first be used to transform the locations of the nodes of the computer model in a computer model space to locations in patient space. For example, the initial correspondence function can be used to map the deformed nodes into the patient space. Afterwards, at block 508, the deformation displacement vector field values can be used to deform the computer model in patient space and thus provide a fit to the surface data in patient space. Consequently or in combination with the deformation or transformation of the locations of the nodes of computer model at block 508, the nodes of the computer model can also be associated with reverse deformation values at block 510 (i.e., the negative values of the deformation displacement vector field values received).

The steps described above will be generally sufficient for enabling an IGS to place a cursor representing the location of an instrument/object in the proper location when the position of the instrument/object is within a portion of the non-rigid structure. However, outside the non-rigid structure, the location would quickly revert back to essentially a rigid transformation. This can result in the cursor position jumping erratically as the instrument/object in moved. Thus, prior to any transformation of instrument/object location, the various embodiments of the invention provide for calculating additional reverse displace field values in regions of patient space surrounding the deformed computer model at block 512. These additional values can be computed by include solving a partial differential equation that, describes the process of diffusion explicitly using a finite difference method on the natural voxel grid in patient, space prior to the transformation of instrument location coordinates. In this embodiment, all voxels associated with deformed computer model have undeforming vector displacements associated with them. Taking an individual displacement, grid, e.g. the medial-to-lateral displacement direction, the aforementioned diffusion method can be used whereby the medial-to-lateral displacements are fixed within the organ but allowed to numerically diffuse to create an envelope surrounding the computer model. Thus, an additional, small envelope of non-rigid transformations is defined in regions just outside the surfaces of the non-rigid structure. The envelope thus defines a region that smoothly transitions from the reverse flow field values of the deformed computer model in patient space and the rigid transforms elsewhere in patient space. Accordingly, if an instrument/object is located near the surface of the non-rigid structure, its transformation into the original computer model space will be based on the envelope rather than the rigid transformation. Thus, a mapping is generated to allow for a smooth local transform when a stylus/object is used within the IGS system both within and near the physical organ surface. In some embodiments of the invention, the partial differential equation can be a diffusion equation. However, the invention is not limited in this regard and other types of partial differential equations or interpolative methods can be used to form the envelope in the various embodiments of the invention such as averaging schemes or a neighborhood functional form.

Once the computer model and patient space is processed at blocks 506-512, transformation of the instrument/object location into image space can begin starting at block 514.

First, at block 512, the reverse flow field values from block 508 and 512 are used to initially transform the coordinates of the instrument location in patient, space. Afterwards, at block 514, this location data for the instrument/object in patient space is further transformed into location data in computer model space. More specifically, the location of the instrument/object in physical space is transformed by the reverse displacement field. Once performed, the instrument/object location has been effectively undeformed. Block 516 can then apply the transform from patient-space to image-space, i.e. the rigid alignment transform associated with step 104 of FIG. 1 (or the appropriate rigid transform depending on the embodiment, of FIG. 1). Once the transformations at blocks 514 and 516 are completed, coordinates for an instrument/object in image space are known and appropriate image data can be determined in block 518. In particular, the relationship between the deformed organ(s) in patient-space as captured by instrumentation can be used to adjust nodes of the computer model such that a complete path between the voxels of the image data and the location of the instrument/object can be derived for display in image space.

Afterwards, at block 520, the image data and indicia of the instrument/object location can be displayed during the IGS procedure. In the various embodiments of the invention, the image data and indicia for the instrument/object can be displayed in a two-dimensional or three-dimensional format. In the case of a two-dimensional format, the instrument location in image space can be used to identify the appropriate cardinal image slices in the image guided display and the cursor position. Afterwards, the image data and cursor can be displayed at block 520. Once the correspondence of instrument/object physical position to that of the particular voxel in image space, any number of standard displays can be generated. For example, the standard cardinal image displays could be used. However, any and all other information expressed in the image space could be rendered with some relationship to the cursor. In addition, while instrument/object location is important, the path or trajectory from the current location to a neighboring location is likely to be important. In order to provide such information, other objects or locations on the surface or nearby may need to be transformed to image-space to provide for accurate navigation. In this case the transform steps could be modified such that the location/object and neighboring portions are deformed and rigidly transformed to their appropriate positions in image-space thus ensuring that when navigating from a current location to a neighboring location in physical space that the corresponding path image space is accurate. The method 500 then proceeds to block 520 to continue previous processing, including repeating method 500 when the instrument is moved.

Figure 6:
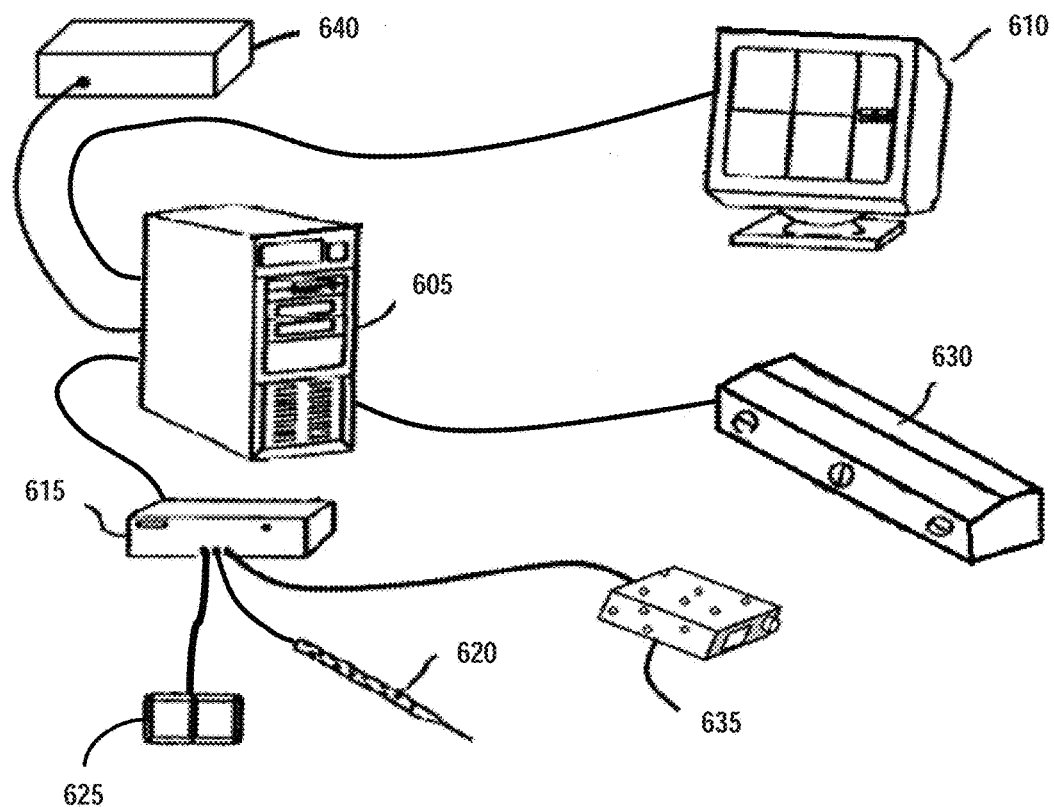
FIG. 6 shows an exemplary hardware system configuration in accordance with an embodiment of the invention.

An exemplary hardware configuration for performing one or more of the tasks identified above with respect to FIGS. 1-5 is shown below in FIG. 6, FIG. 6 shows an exemplary hardware system configuration 600 in accordance with an embodiment of the invention. As shown in FIG. 6, system 600 can include an image/data processor 605, a display monitor 610, and an IGS controller 615. The IGS controller can be coupled to an optical tracking sensor which consists of sensing optical cameras 630, and emitters 620, 625, and 635. Further, the IGS controller 615 can be coupled to one or more emitters that can serve as instruments such as 620, and 635. 640 is a separate computation node controller that interfaces to the image/data processor 605 for the purpose of non-rigid deformation correction and the embodiment of related processes Although the various components are shown as separate, discrete components, the invention is not limited in this regard. For example, the IGS controller 615, the image data processor 605, and the computation node controller 640 can be integrated into a single system. Similarly, depending on the nature of correction, the computation node controller 640 could be separated into multiple computation node controllers networked together.

System 600 operates as follows. First, emitter 625 is often affixed to the patient, or supporting surgical instrumentation. This could be replaced by providing a fixed camera mount (i.e. fix 630) within the operating room. Sensor 630 is used to determine the location of all emitters within the operating room (to include optical stylus 620, or potentially a laser range scanner 635). Emitter 620, or 635 could be used to detect a surface, or visible structure of a non-rigid organ or the location of an instrument. However, the invention is not limited in this regard and more than one sensing system can be used to provide surface data and/or instrument/object position data. An example of a system for generating surface data is a laser-range scanner system, such as the RealScan 3D system produced by 3D Digital Corporation of Danbury, Conn. or a similar system custom designed by Pathfinder Therapeutics Inc. of Nashville, Tenn. Such systems are capable of capturing three-dimensional topographic surface data as well surface texture mapping using an array of data points. For example, in one embodiment, a scanning field of 500 horizontal by 512 vertical points can be acquired in 5-10 seconds and used to generate surface data of exposed surfaces during IGS procedures. In some embodiments, such a system can be tracked in the operating room space using a digitization system and calibrated using phantoms with separate independent digitization. 635 would represent the result of their use. One advantage of this laser-range scanner system over other surface digitization techniques is the capability of capturing feature-rich texture maps of the surface as well as the topographical characteristics. Such texture map data generally facilitates the segmentation, i.e. extraction, of the liver surface for alignment to preoperative imaging. Other embodiments could use a tracked ultrasound probe which could acquire external and/or interior surface data. The data could be used to extract any number of boundary data to include external and/or interior surface structures for use in the alignment process.

In operation, system 600 operates as follows. Prior to surgery, relevant data regarding the preoperative organ 102 would be transmitted to the computation node controller 640 or would have been processed on the controller 615. Upon collection of surface data from digitization equipment, like that of 620 and 635, the image/data processor 605 transmits that data as well as any other relevant intraoperative information to the computation node controller 640. Using the computer model, the computation node controller 640 completes the rigid alignment of the computer model to the surface data, as described in FIG. 1, followed by the non-rigid alignment of the computer model to the surface data, as described in FIGS. 1 and 2. Data/image processor 605 may also perform transformations on the data. As described above, a local transformation may also be required. In such cases, the computation node controller 640 can generate such deformed and adjusted maps, as described above with respect to FIG. 5. The map can then be used to perform IGS procedures either by transforming points on the computation node controller 640, or by providing the proper mapping function to the data/image processing unit 605 and allowing it to apply the proper transform for the IGS display 610.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Figure 7:
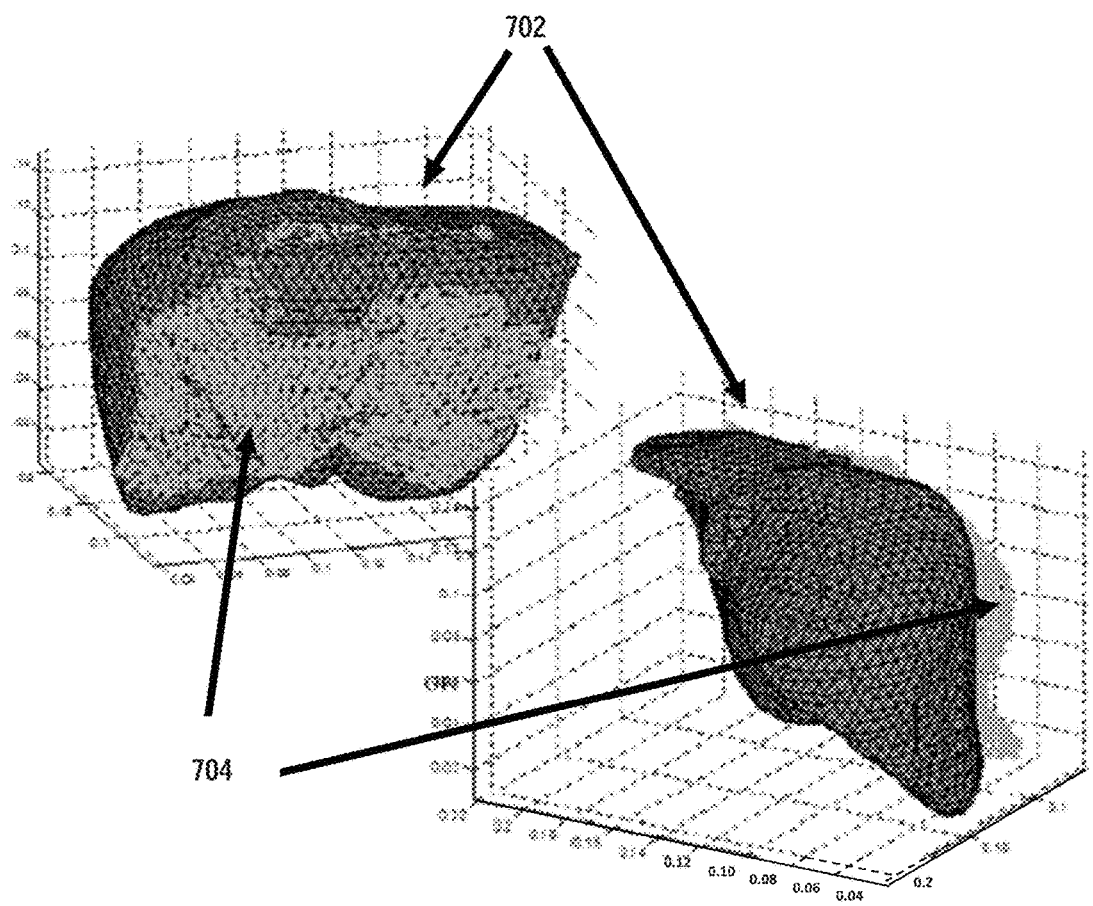
FIG. 7 shows the results of an initial rigid alignment of the computer model and surface data in accordance with an embodiment of the invention.
Figure 8:
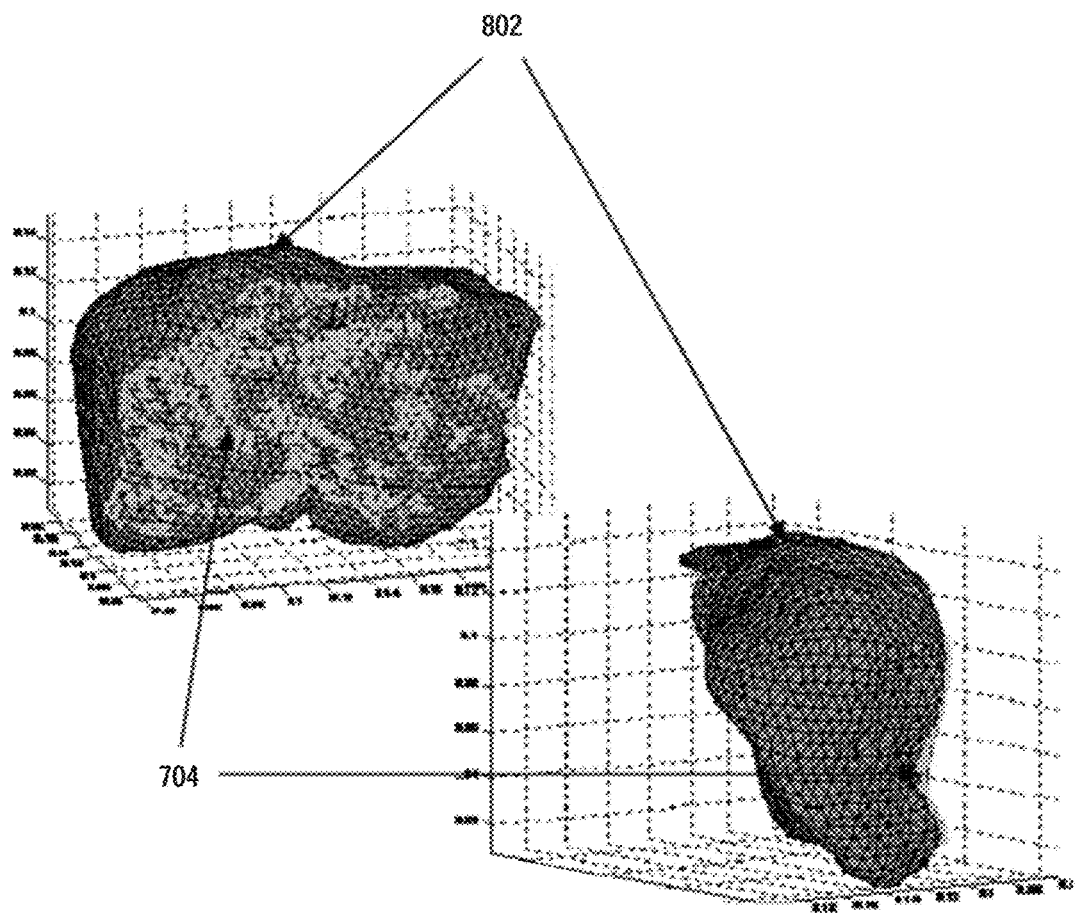
FIG. 8 shows the results of a non-rigid alignment of the computer model and surface data in FIG. 7 in accordance with an embodiment of the invention.
Figure 9:
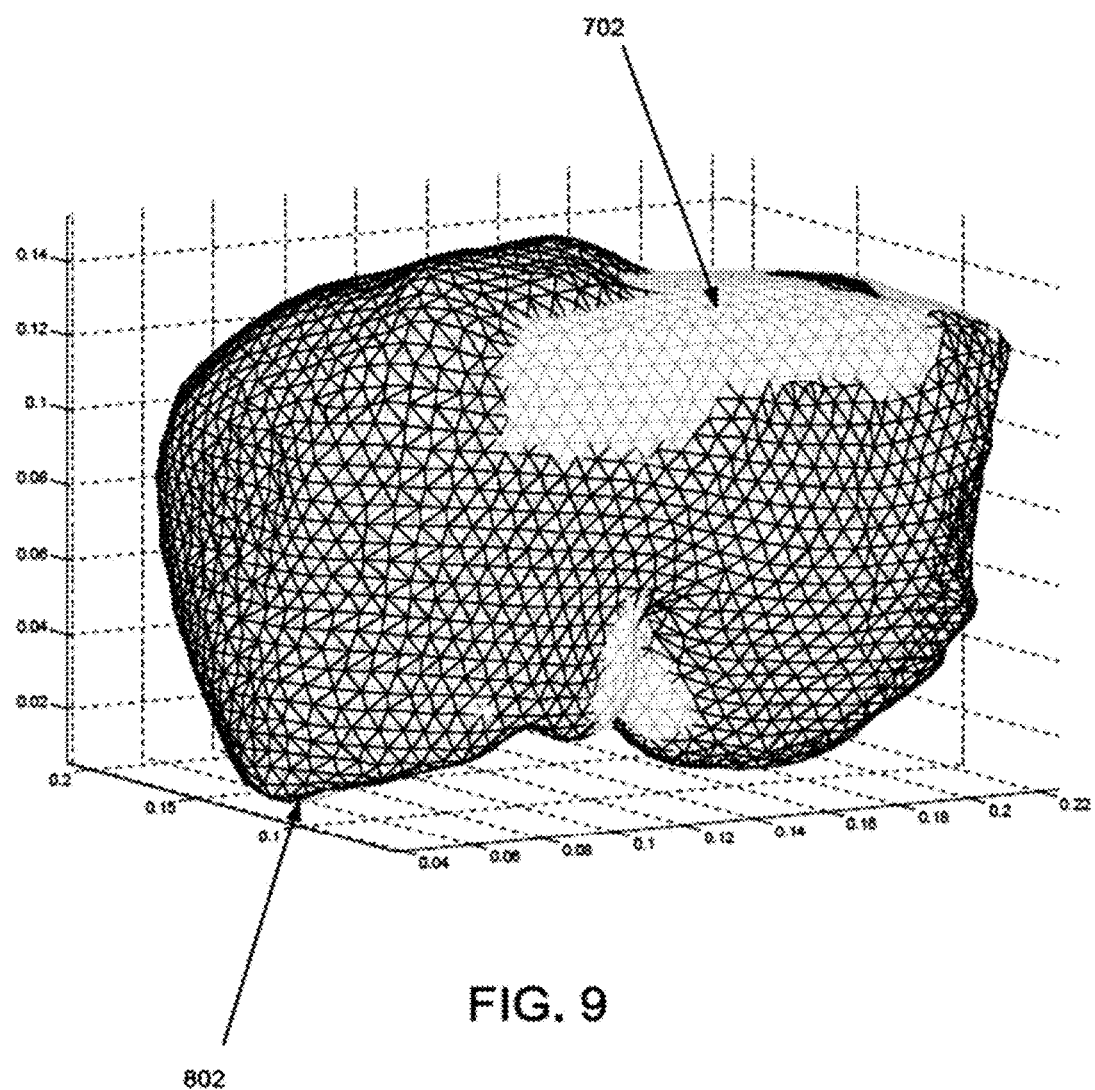
FIG. 9 is an overlay of the computer model shown in FIG. 7 and the deformed computer model shown in FIG. 8.

An exemplary system was constructed, similar to that illustrated in FIG. 6. In particular, a Stealth Model No. LPC-650-T9500-64GF-04G-6-E-00 Little PC (Computer) was configured to operate as the computation node controller 640. The controller was used to provide a rigid and non-rigid alignment of a computer model and surface data of a liver in accordance with an embodiment of the invention as well as the preoperative processing components associated with 102. FIG. 7 shows the results of an initial rigid alignment of the computer model 702 (black mesh) and surface data 704 (gray points). These results were obtained using a salient feature weighting registration method. FIG. 8 shows the results of a non-rigid alignment in accordance with an embodiment of the invention. These results were obtained using a finite element method in approximately 12 iterations. As shown in FIG. 8, the deformed computer model 802 (black mesh) now is in greater agreement with the points of the surface data 704 (gray points). The execution of the realization and result shown in data 704 represents a mean closest point distance between the model and surface data of 4.7+/−3.0 mm prior to correction on the computation node controller. After the computation node controller execution of the invention reported herein, the closest point distance became 1.5+/−0.8 mm. The amount of deformation of the computer model is shown in FIG. 9, where the original computer model data and the deformed computer model data are overlaid. In FIG. 9, the original computer model 702 is shown by the gray mesh and the deformed computer model is shown by the black mesh.

Figure 10:
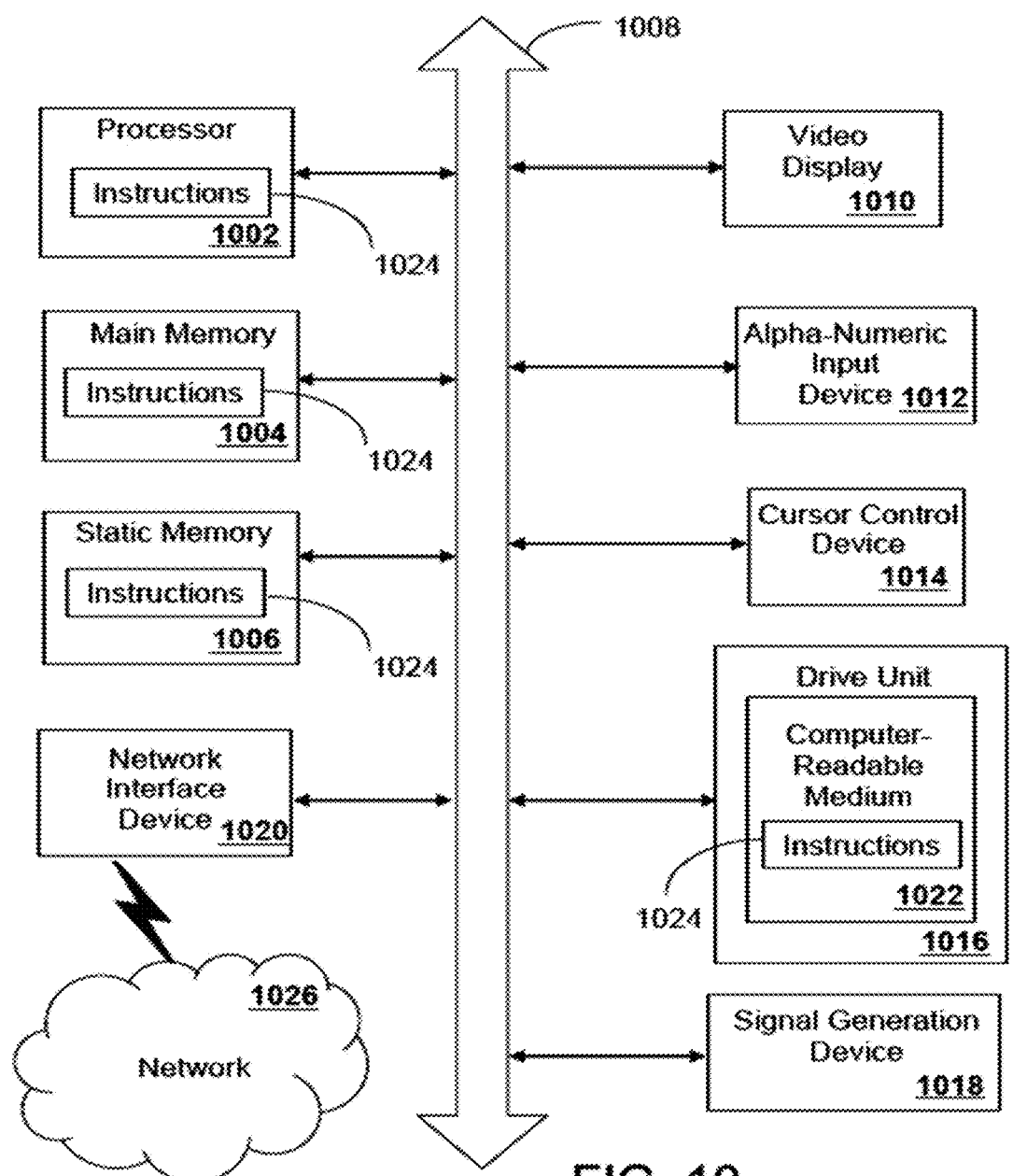
FIG. 10 is a schematic diagram of a computer system for executing a set of instructions that, when executed, can cause the computer system to perform one or more of the methodologies and procedures described above.

FIG. 10 is a schematic diagram of a computer system 1000 for executing a set of instructions that, when executed, can cause the computer system to perform one or more of the methodologies and procedures described above. For example, the architecture of computer system 1000 can be used to describe the architecture of one or more components of FIG. 6. In some embodiments, the computer system 1000 operates as a standalone device. In other embodiments, the computer system 1000 can be connected (e.g., using a network) to other computing devices. In a networked deployment, the computer system 1000 can operate in the capacity of a server or a client developer machine in server-client developer network environment, or as a peer machine in a peer-to-peer (or distributed) network environment. In some embodiments, the system could be a plug-in card to the guidance system.

The machine can comprise various types of computing systems and devices, including a server computer, a client user computer, a personal computer (PC), a tablet PC, a laptop computer, a desktop computer, a control system, a network router, switch or bridge, or any other device capable of executing a set of instructions (sequential or otherwise) that specifies actions to be taken by that device. It is to be understood that a device of the present disclosure also includes any electronic device that, provides voice, video or data communication. Further, while a single computer is illustrated, the phrase "computer system" shall be understood to include any collection of computing devices that individually or jointly execute a set (or multiple sets) of instructions to perform any one or more of the methodologies discussed herein.

The computer system 1000 can include a processor 1002 (such as a central processing unit (CPU), a graphics processing unit (GPU, or both), a main memory 1004 and a static memory 1006, which communicate with each other via a bus 1008. The computer system 1000 can further include a display unit 1010, such as a video display (e.g., a liquid crystal display or LCD), a flat panel, a solid state display, or a cathode ray tube (CRT)). The computer system 1000 can include an input device 1012 (e.g., a keyboard), a cursor control device 1014 (e.g., a mouse), a disk drive unit 1016, a signal generation device 1018 (e.g., a speaker or remote control) and a network interface device 1020.

The disk drive unit 1016 can include a computer-readable storage medium 1022 on which is stored one or more sets of instructions 1024 (e.g., software code) configured to implement, one or more of the methodologies, procedures, or functions described herein. The instructions 1024 can also reside, completely or at least partially, within the main memory 1004, the static memory 1006, and/or within the processor 1002 during execution thereof by the computer system 1000. The main memory 1004 and the processor 1002 also can constitute machine-readable media.

Dedicated hardware implementations including, but not limited to, application-specific integrated circuits, programmable logic arrays, and other hardware devices can likewise be constructed to implement the methods described herein. Applications that, can include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the exemplary system is applicable to software, firmware, and hardware implementations.

In accordance with various embodiments of the present disclosure, the methods described herein can be stored as software programs in a computer-readable storage medium and can be configured for running on a computer processor. Furthermore, software implementations can include, but are not limited to, distributed processing, component/object distributed processing, parallel processing, virtual machine processing, which can also be constructed to implement the methods described herein.

The present disclosure contemplates a computer-readable storage medium containing instructions 1024 or that receives and executes instructions 1024 from a propagated signal so that a device connected to a network environment 1026 can send or receive voice and/or video data, and that can communicate over the network 1026 using the instructions 1024. The instructions 1024 can further be transmitted or received over a network 1026 via the network interface device 1020.

While the computer-readable storage medium 1022 is shown in an exemplary embodiment to be a single storage medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any device that is capable of storing a set of instructions for execution by the machine and that cause the machine to perform any one or more of the methodologies of the present disclosure.

The term "computer-readable medium" shall accordingly be taken to include, but not be limited to, solid-state memories such as a memory card or other package that houses one or more read-only (non-volatile) memories, random access memories, or other re-writable (volatile) memories; magneto-optical or optical medium such as a disk or tape; as well as carrier wave signals such as a signal embodying computer instructions in a transmission medium; and/or a digital file attachment to e-mail or other self-contained information archive or set of archives considered to be a distribution medium equivalent to a tangible storage medium. Accordingly, the disclosure is considered to include any one or more of a computer-readable medium or a distribution medium, as listed herein and to include recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

Applicants present certain theoretical aspects below that, are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. For example, although the various embodiments are primarily described with respect to a transformation of coordinates or locations in a patient, space to a computer model space or an image space, the invention is not limited in this regard. Rather, the systems and method described herein are equally applicable for determining coordinates or locations in a patient space based on locations of interest in the computer model space or the image space. Such locations can be identified by providing coordinates or locations relative to any fiducial markers or other reference locations associated with the non-rigid structures in the patient space. Such a configuration can be utilized, for example, to identify an initial location for beginning a procedure or to otherwise assist the user in identifying or visualizing structures in the patient space. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for collecting and processing physical space data for use while performing an image-guided surgical (IGS) procedure, the method comprising:

obtaining a preoperative image of a surface of a non-rigid structure of interest in a patient, wherein the preoperative image was acquired during a preoperative presentation of the structure;

during an intraoperative presentation of the structure, generating in patient space, via digitization equipment of an IGS system, partial surface data extending over a portion of the surface, wherein the portion, as presented intraoperatively, is less than 50% of the surface and wherein during the intraoperative presentation the surface is deformed relative to the preoperative presentation;

performing, via a processor of the IGS system, a rigid alignment, in the patient space, of the partial surface data to a computer model corresponding to the preoperative image, the computer model comprising a plurality of nodes, the plurality of nodes extending over all of the surface of the non-rigid structure;

computing, via the processor of the IGS system, a deformation of the computer model, wherein the deformation provides a non-rigid alignment, in the patient space, of said computer model and the partial surface data, said deformation computed using boundary conditions calculated for each of the plurality of nodes of said computer model, said boundary conditions calculated using a kernel function and spatial difference values for each of the plurality of nodes derived from said rigid alignment;

applying said deformation of the computer model to the preoperative image and thereby computing a modified image; and displaying, at a display of the IGS system, the modified image.

2. The method of claim 1, wherein said computing further comprises:

calculating the spatial difference values between the partial surface data and corresponding portions of the computer model using a correspondence function;

selecting a zero value for the spatial difference values outside the corresponding portions of the computer model;

assigning weights to the spatial difference values for each of the plurality of nodes using the kernel function;

computing the boundary conditions using the spatial difference values and said assigned weights, the boundary conditions for each one of the plurality of nodes computed as a weighted average of the one of the plurality of nodes and surrounding ones of the plurality of nodes;

generating displacement field vector values for each of the plurality of nodes of said computer model using the boundary conditions;

producing an updated computer model using the displacement field vector values;

updating the correspondence function using the updated computer model;

recalculating the spatial difference values between the partial surface data and corresponding portions of the computer model using the updated correspondence function;

repeating the calculating, selecting, assigning, computing, generating, producing, updating, and recalculating steps if the set of spatial difference values fail to meet convergence criteria; and outputting the updated computer model.

3. The method of claim 2, wherein said generating said displacement field vector values further comprises accumulating said displacement field vector values from each time the generating step is performed, and wherein said outputting further comprises outputting an accumulated displacement vector field comprising a combination of said accumulated displacement field vector values.

4. The method of claim 2, further comprising selecting said convergence criteria to be at least one of a minimum threshold value for the set of spatial difference values or a minimum difference value between a current one of the set of spatial difference values and a previous one of the set of spatial difference values, wherein said selecting is performed before said updating, after said updating, or after a pre-defined number of iterations.

5. The method of claim 1, wherein said computing further comprises:

receiving a location of an object or tool in said patient space;

computing reverse deformation displacement vector field values for each of the plurality of nodes of said computer model corresponding to the deformation;

calculating an envelope of additional reverse deformation vector field values for a portion of said patient space surrounding said deformed computed model;

transforming said location into a computer model space of said computer model using said rigid alignment and said reverse deformation displacement vector field values to yield a transformed location; and calculating coordinates of the object or tool in an image space of said preoperative image from said transformed location of said object or tool.

6. The method of claim 5, further comprising:

displaying said preoperative image; and displaying indicia of said object location in said image space of the preoperative image corresponding to said calculated coordinates in said image space.

* * * * *

UNITED STATES PATENT AND TRADEMARK OFFICE
CERTIFICATE OF CORRECTION

PATENT NO. : 9,767,573 B2
APPLICATION NO. : 13/574624
DATED : September 19, 2017
INVENTOR(S) : Miga et al.

Page 1 of 1

It is certified that error appears in the above-identified patent and that said Letters Patent is hereby corrected as shown below:

In the Specification

In Column 1, after the section entitled STATEMENT REGARDING FEDERALLY SPONSORED RESEARCH, Lines 17-20 should be replaced with the following:
--This invention was made with government support under grant numbers EB007694 and CA162477 awarded by the National Institutes of Health. The government has certain rights in the invention.--

Signed and Sealed this
Tenth Day of December, 2019

Andrei Iancu
*Director of the United States Patent and Trademark Office*